United States Patent [19]
Callahan et al.

[11] Patent Number: 6,117,910
[45] Date of Patent: Sep. 12, 2000

[54] BICYCLIC FIBRINOGEN ANTAGONISTS

[75] Inventors: James Francis Callahan, Philadelphia; Richard McCulloch Keenan, Malvern; Chet Kwon, King of Prussia; James Martin Samanen, Phoenixville, all of Pa.

[73] Assignee: SmithKline Beecham Corporation, Philadelphia, Pa.

[21] Appl. No.: 08/875,361

[22] PCT Filed: Dec. 7, 1995

[86] PCT No.: PCT/US95/15937

§ 371 Date: Jun. 13, 1997

§ 102(e) Date: Jun. 13, 1997

[87] PCT Pub. No.: WO96/18602

PCT Pub. Date: Jun. 20, 1996

Related U.S. Application Data

[60] Provisional application No. 08/355,355, Dec. 13, 1994, abandoned.

[51] Int. Cl.[7] .................... A61K 31/16; C07D 217/00
[52] U.S. Cl. .................... 514/614; 564/147; 546/147; 514/311
[58] Field of Search ................ 546/147; 560/20; 562/433, 439, 440, 442; 514/311, 313, 314, 513, 569, 570, 614; 564/147

[56] References Cited

FOREIGN PATENT DOCUMENTS

| | | |
|---|---|---|
| 0381033 | 1/1990 | European Pat. Off. . |
| 0478363 | 9/1991 | European Pat. Off. . |
| 0548949 | 6/1993 | European Pat. Off. . |
| 0 635 492 A1 | 7/1994 | European Pat. Off. . |
| WO 89/05150 | 6/1989 | WIPO . |
| 0372486 | 12/1989 | WIPO . |
| WO 92/07568 | 5/1992 | WIPO . |
| WO 93/00095 | 1/1993 | WIPO . |
| WO 94/29273 | 12/1994 | WIPO . |

*Primary Examiner*—Zinna Northington Davis
*Attorney, Agent, or Firm*—Mary E. McCarthy; Stephen Venetianer; Charles M. Kinzig

[57] ABSTRACT

This invention relates to compounds of the formula:

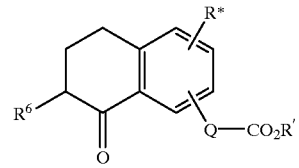

which are effective for inhibiting platelet aggregation, pharmaceutical compositions for effecting such activity, and a method for inhibiting platelet aggregation.

6 Claims, No Drawings

BICYCLIC FIBRINOGEN ANTAGONISTS

This application is a 371 of PCT/US95/15937 filed Dec. 7, 1995 which is a continuation of U.S. Ser. No. 08/355,355 filed Dec. 13, 1994, now abandoned.

FIELD OF THE INVENTION

This invention relates to novel bicyclic compounds which inhibit platelet aggregation, pharmaceutical compositions containing the compounds and methods of using the compounds.

BACKGROUND OF THE INVENTION

Platelet aggregation is believed to be mediated primarily through the fibrinogen receptor, or GPIIb-IIIa platelet receptor complex, which is a member of a family of adhesion receptors referred to as integrins. It has been found that frequently the natural ligands of integrin receptors are proteins which contain an Arg-Gly-Asp sequence. Von Willebrand factor and fibrinogen, which are considered to be natural ligands for the GPIIb-IIIa receptor, possess an Arg-Gly-Asp (RGD in single letter amino acid code) sequence in their primary structure. Functionally, these proteins are able to bind and crosslink GPIIb-IIIa receptors on adjacent platelets and thereby effect aggregation of platelets.

Fibronectin, vitronectin and thrombospondin are RGD-containing proteins which have also been demonstrated to bind to GPIIb-IIIa. Fibronectin is found in plasma and as a structural protein in the intracellular matrix. Binding between the structural proteins and GPIIb-IIIa may function to cause platelets to adhere to damaged vessel walls.

Linear and cyclic peptides which bind to vitronectin and contain an RGD sequence are disclosed in WO 89/05150 (PCT US88/04403). EP 0 275 748 discloses linear tetra- to hexapeptides and cyclic hexa- to octapeptides which bind to the GPIIb-IIIa receptor and inhibit platelet aggregation. Other linear and cyclic peptides, the disclosure of which are incorporated herein by reference, are reported in EP-A 0 341 915. However, the peptide like structures of such inhibitors often pose problems, such as in drug delivery, metabolic stability and selectivity. Inhibitors of the fibrinogen receptor which are not constructed of natural amino acid sequences are disclosed in EP-A 0 372,486, EP-A 0 381 033 and EP-A 0 478 363. WO 92/07568 (PCT/US91/08166) discloses fibrinogen receptor antagonists which mimic a conformational γ-turn in the RGD sequence by forming a monocyclic seven-membered ring structure. There remains a need, however, for novel fibrinogen receptor antagonists (e.g., inhibitors of the GPIIb-IIIa protein) which have potent in vivo and in vitro effects and lack the peptide backbone structure of amino acid sequences.

The present invention discloses novel bicyclic compounds, including 1,2,3,4-tetrahydroisoquinolines, 1,2,3,4-tetrahydronaphthalenes, and 1-tetralones. These compounds inhibit the GPIIb-IIIa receptor and inhibit platelet aggregation.

SUMMARY OF THE INVENTION

In one aspect this invention is a bicyclic compound comprising a substituted six-membered ring fused to an aromatic six-membered ring as described hereinafter in formula (I).

This invention is also a pharmaceutical composition for inhibiting platelet aggregation or clot formation, which comprises a compound of formula (I) and a pharmaceutically acceptable carrier.

This invention is further a method for inhibiting platelet aggregation in a mammal in need thereof, which comprises internally administering an effective amount of a compound of formula (I).

In another aspect, this invention provides a method for inhibiting reocclusion of an artery or vein in a mammal following fibrinolytic therapy, which comprises internally administering an effective amount of a fibrinolytic agent and a compound of formula (I). This invention is also a method for treating stroke, transient ischemia attacks, or myocardial infarction.

DETAILED DESCRIPTION OF THE INVENTION

This invention discloses bicyclic compounds which inhibit platelet aggregation. The novel bicyclic compounds comprise a six-membered ring fused to an aromatic six-membered ring and having a nitrogen-containing substituent on the six-membered ring and an aliphatic substituent, preferably containing or being an acidic moiety, on the aromatic six-membered ring. The six-membered ring may contain heteroatoms, such as nitrogen, oxygen and sulfur, and the aromatic six-membered ring is carbocyclic. The fused 6—6 ring system is believed to interact favorably with the GPIIb-IIIa receptor and to orient the substituent sidechains on the aromatic six and sthe six-membered rings so that they may also interact favorably with the receptor.

Although not intending to be bound to any specific mechanism of action, these compounds are believed to inhibit the binding of fibrinogen to the platelet-bound fibrinogen receptor GPIIb-IIIa, and may interact with other adhesion proteins via antagonism of a putative RGD binding site.

The compounds of this invention are compounds of formula (I):

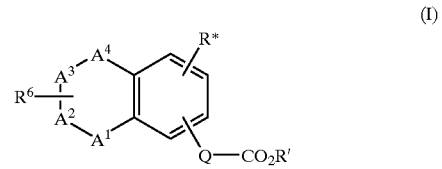

(I)

wherein:

$A^1$ to $A^4$ form an accessible substituted saturated six-membered ring, optionally containing up to two heteroatoms chosen from the group of O, S, and N wherein S and N may be optionally oxidized;

Q is —O(CH$_2$)$_m$—, —NR'C(O)CH$_2$, —CH$_2$CH$_2$—, —CH(CH$_3$)CH$_2$—, —CH=CH—, —NR'CH$_2$—, or —CH$_2$—;

R* is H, Q—CO$_2$R', CO$_2$R', C$_{1-4}$alkyl, C$_{1-4}$alkoxy, C$_{1-4}$alkylthio, hydroxy, halo, NR'R', CN, CONR'R', CF$_3$ or ArC$_{0-4}$alkyl;

$R^6$ is W—(CR'$_2$)$_q$—Z—(CR'R$^7$)$_r$—U—(CR'$_2$)$_s$—V—;

$R^7$ is H, C$_{1-4}$alkyl or —NR'R";

$R^8$ is R', —CF$_3$, —SR', or —OR';

$R^9$ is R', C(O)R', CN, NO$_2$, SO$_2$R' or C(O)OR$^{10}$;

$R^{10}$ is H, C$_{1-6}$alkyl or Ar—C$_{0-4}$alkyl;

R' is H, C$_{1-6}$alkyl, C$_{3-7}$cycloalkyl—C$_{0-4}$alkyl or Ar—C$_{0-4}$alkyl;

R" is R', —C(O)R' or —C(O)OR$^{10}$;

U and V are absent or CO, CR'$_2$, C(=CR'$_2$), S(O)$_n$, O, NR', CR'OR', CR'(OR")CR'$_2$, CR'$_2$CR'(OR"), C(O)

CR'$_2$, CR'$_2$C(O), CONR', NR'CO, OC(O), C(O)O, C(S)
O, OC(S), C(S)NR', NR' C(S), S(O)$_n$NR', NR'S(O)$_n$,
N=N, NR'NR', NR'CR'$_2$, NR'CR'$_2$, CR'$_2$O, OCR'$_2$, or
CR'=CR', provided that U and V are not simultaneously absent;

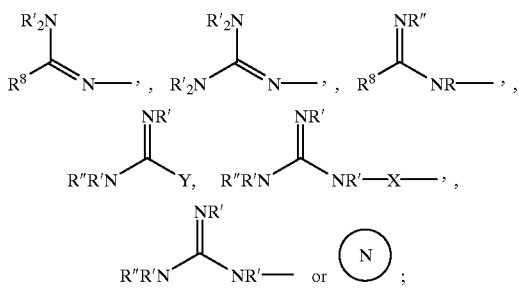

X is N=CR', C(O) or O;

Y is absent, S or O;

Z is (CH$_2$)$_t$, Het, Ar or C$_{3-7}$cycloalkyl;

m is 1 or 2;

n is 0 to 3;

q is 0 to 3;

r is 0 to 2;

s is 0 to 2; and t is 0 to 2; or
pharmaceutically acceptable salts thereof.

Also included in this invention are pharmaceutically acceptable addition salts, complexes or prodrugs of the compounds of this invention. Prodrugs are considered to be any covalently bonded carriers which release the active parent drug according to formula (I) in vivo.

In cases wherein the compounds of this invention may have one or more chiral centers, unless specified, this invention includes each unique nonracemic compound which may be synthesized and resolved by conventional techniques. In cases in which compounds have unsaturated carbon-carbon double bonds, both the cis (Z) and trans (E) isomers are within the scope of this invention. In cases wherein compounds may exist in tautomeric forms, such as keto-enol tautomers,

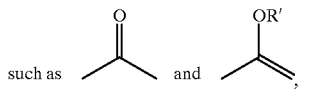

such as       and and tautomers of guanidine-type groups, such as

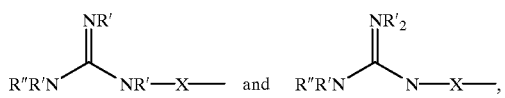

each tautomeric form is contemplated as being included within this invention whether existing in equilibrium or locked in one form by appropriate substitution with R'. The meaning of any substituent at any one occurrence is independent of its meaning, or any other substituent's meaning, at any other occurrence, unless specified otherwise.

With reference to formula (1), suitably,

A$^1$ is CR$^1$R$^{1'}$, CR$^1$, NR$^1$, O or S(O)$_x$;

A$^2$ is CR$^2$R$^{2'}$ or NR$^2$;

A$^3$ is CR$^3$R$^{3'}$ or NR$^3$;

A$^4$ is CR$^4$R$^{4'}$ or CR$^4$;

R$^1$ and R$^{1'}$ are each hydrogen or together are =O;

R$^2$ and R$^{2'}$ are each hydrogen or R$^2$ is R$^6$ and R$^{2'}$ is absent or present as hydrogen;

R$^3$ and R$^{3'}$ are each hydrogen or R$^3$ is R$^6$ and R$^{3'}$ is absent or present as hydrogen;

R$^4$ and R$^{4'}$ are each hydrogen or together are =O and;

x is 0 to 2.

More suitably, A$^1$ is CR$^1$R$^{1'}$, NR$^1$, O or S; A$^2$ is CR$^2$R$^{2'}$ or NR$^2$; A$^3$ is CR$^3$R$^{3'}$; A$^4$ is CR$^4$R$^{4'}$ or NR4; R$^2$ or R$^3$ is R$^6$; and R$^6$ is W—(CR'$_2$)$_q$—Z—(CR'R$^{10}$)$_r$—U.

Preferably, A$^1$ is CR$^1$R$^{1'}$; A$^2$ is CR$^2$R$^{2'}$ or NR$^2$; A$^3$ is CR$^3$R$^{3'}$; and A$^4$ is CR$^4$R$^{4'}$.

Suitably, (CR'R$^7$)$_r$—U—(CR'$_2$)$_s$—V is CO, CONR', NR'CO, CH$_2$, CH$_2$CHOH, CHOHCH$_2$, CH$_2$CH$_2$, CH$_2$O, OCH$_2$, O, CH=CH, or C≡C.

More suitably, Q is —O(CH$_2$)$_n$—, —NHC(O)CH$_2$—, or —C(O)NHCH$_2$—; Z is phenyl, a six-membered Het or (CH$_2$)$_t$; and W is R'$_2$N, H$_2$NC(=NH), H$_2$NC(=NH)NH or ⓝ.

In a preferred embodiment, A$^1$ is C=O, A$^2$ is CHR$^6$, A$^3$ is CH$_2$ and A$^4$ is CH$_2$.

In another preferred embodiment, A$^1$, A$^2$, and A$^4$ are CH$_2$ and A$^3$ is CHR$^6$.

In another preferred embodiment, A$^1$, A$^3$, and A$^4$ are CH$_2$ and A$^2$ is NR$^6$.

In a more specific embodiment, A$^1$ is C=O; A$^2$ is NR$^2$; A$^3$ is CR$^3$R$^{3'}$; A$^4$ is CR$^4$R$^{4'}$; R$^2$ is CH$_2$CO$_2$H or CH$_2$CH$_2$CO$_2$H; R$^3$,R$^{3'}$ is H,H; R$^4$, R$^{4'}$ is H,H; Z is phenyl, a six-membered Het or (CH$_2$)$_t$; W is R'$_2$N, H$_2$NC(=NH), H$_2$NC(=NH)NH or ⓝ; and (CR'R$^{10}$)$_r$—U—(CR'$_2$)$_s$—V is (CR'R$^7$)$_r$—U— or —U—(CR'$_2$)$_s$, (e.g., V is absent and s is 0 and one of s and r are 0) wherein U is CH(NR'R")CONH, NR'CO, CONR', CR'=CR', C≡C, O, CO or CH$_2$.

Representative compounds of this invention are given by each of formulas (II)–(IV):

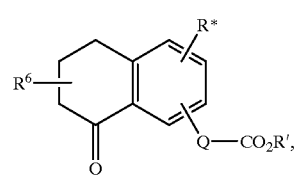

(II)

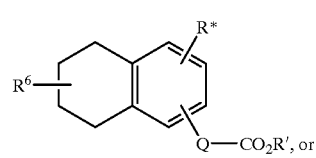

(III)

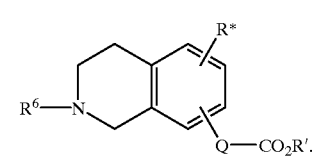

(IV)

Particular examples of $R^6$ are:

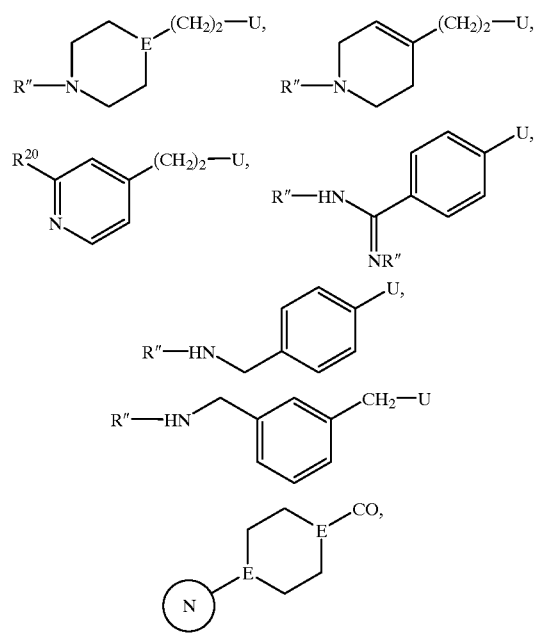

$R''HNC(=NH)NH—(CH_2)_3(CHR^7)—U$, and $R''HN—(CH_2)_5—U$ wherein E is N or CH, $R^{20}$ is hydrogen, amino, mono or di-$C_{1-4}$alkylamino, hydroxy or $C_{1-4}$alkyl, and U is NR'CO, CONR', $(CH_2)CO$, $CH=CH,$, $CH_2O$, $OCH_2$, $CH_2$, and $(CH_2)_2$.

Preferred compounds of this inventions are:

2-[[4-(aminoiminomethyl)benzoyl]amino]-6-acetyloxy-1,2,3,4-tetrahydronaphthalene;

2-[[4-(aminoiminomethyl)benzoyl]amino]-6-acetyloxy-1-tetralone;

2-(4-aminomethylbenzyl)-7-amidomalonyl-1-tetralone; and

N-[(4-aminoiminomethyl)benzoyl]-6,7-diacetyloxy-1,2,3,4-tetrahydroisoquinoline;

or a pharmacetuically acceptable salt thereof.

In the above description of formula (I), preferably only one of $A^1$ to $A^4$ are substituted by $R^6$, and W represents a nitrogen-containing group which is capable of making a hydrogen bond. Preferably W is a basic nitrogen moiety. It is also preferred that 10–15 (most preferably about 13) intervening covalent bonds via the shortest intramolecular path will exist between the group $CO_2R'$ of formula (I) and a terminal basic nitrogen moiety of W for optimal spacing between these groups, and the moieties U, V and Z, and the alkyl spacers represented by q, r and s, are chosen accordingly.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem.*, 158, 9 (1984).

Arg refers to arginine, MeArg refers to $N^\alpha$-methylarginine, HArg refers to homoarginine, NArg refers to norarginine, $(Me_2)$Arg refers to N',N"-dimethyl arginine, $(Et_2)$Arg refers to N',N'-diethyl arginine and Orn refers to ornithine. These radicals are suitable components of the substituent $R^6$. $N^\alpha$-Substituted derivatives of these amino acid are also useful in this invention. Representative methods for preparing α-substituted derivatives are disclosed in U.S. Pat. No. 4,687,758; Cheung et al., *Can. J. Chem.*, 55, 906 (1977); Freidinger et al., *J. Org. Chem.*, 48, 77, (1982); and Shuman et al., PEPTIDES: PROCEEDINGS OF THE 7TH AMERICAN PEPTIDE SYMPOSIUM, Rich, D., Gross, E., Eds, Pierce Chemical Co., Rockford, Ill.,617 (1981), which are incorporated herein by reference.

$C_{1-4}$alkyl as applied herein is meant to include methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof. $C_{0-4}$alkyl and $C_{0-6}$alkyl additionally indicates that no alkyl group need be present (e.g., that a covalent bond is present).

Ar, or aryl, as applied herein, means phenyl or naphthyl, or phenyl or naphthyl substituted by one to three substituents selected from the group consisting of $C_{1-4}$alkyl, $C_{1-4}$alkoxy, $C_{1-4}$alkthio, trifluoroalkyl, OH, F, Cl, Br and I.

Het, or heterocycle, indicates an optionally substituted five or six-membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazole, benzopyran, benzothiophene, furan, imidazole, indoline, morpholine, piperidine, piperazine, pyrrole, pyrrolidine, tetrahydropyridine, pyridine, thiazole, thiophene, quinoline, isoquinoline, and tetra- and perhydro- quinoline and isoquinoline. A six membered ring heterocycle containing one or two nitrogens, such as piperidine, piperazine, tetrahydropyridine and pyridine, are preferred heterocycles for the moiety Z. Any accessible combination of up to three substituents, such as chosen from $C_{1-4}$alkyl, $C_{1-4}$alkoxy, $C_{1-4}$alkthio, trifluoroalkyl, OH, F, Cl, Br and I, on the Het ring that is available by chemical synthesis and is stable is within the scope of this invention. A six membered monocyclic ring heterocycle ("six-membered Het") containing one or two nitrogens, such as piperidine, piperazine, tetrahydropyridine and pyridine, are preferred heterocycles for the moiety Z.

$C_{3-7}$cycloalkyl refers to an optionally substituted carbocyclic system of three to seven carbon atoms, which may contain up to two unsaturated carbon-carbon bonds. Typical of $C_{3-7}$cycloalkyl are cyclopropyl, cyclobutyl, cyclopentyl, cyclopentenyl, cyclohexyl, cyclohexenyl and cycloheptyl. Any combination of up to three substituents, such as chosen from $C_{1-4}$alkyl, $C_{1-4}$alkoxy, $C_{1-4}$alkthio, trifluoroalkyl, OH, F, Cl, Br and I, on the cycloalkyl ring that is available by conventional chemical synthesis and is stable, is within the scope of this invention.

An accessible substituted six-membered ring as referred to herein is any saturated six-membered ring which (i) is substituted by $R^6$, wherein the substituent may be present on any atom or heteroatom that results in a stable structure, and (ii) contains up to two heteroatoms selected from the group of N, O and S, wherein S and N may optionally be oxidized, and (iii) is stable and may be synthesized by one skilled in the chemical arts in a form fused via two adjacent ring carbon atoms to a phenyl ring. Typical of accessible six-membered rings are the common saturated rings of cyclohexane, piperidine, piperazine, morpholine and thiomorpholine. Preferably, no two adjacent atoms in the six-membered ring are simultaneously heteroatoms.

Representative bicyclic rings formed by the combination of the accessible phenyl and the six-membered rings are: tetralin, tetrahydroquinoline, tetrahydroisoquinoline, tetrahydroquinazoline, 3,4-dihydro-2H-1,4-benzoxazine, and 3,4-dihydro-2-H-1,4-benzothiazine. Piperidine is a preferred accessible six-membered ring. Thus a preferred bicyclic ring system is the 1,2,3,4-tetrahydroisoquinoline system. Cyclohexane is another preferred accessible six-membered ring system. Thus a second preferred bicyclic ring system is the tetrahydronaphthalene ring system.

It will be understood that, with respect to $A^1$–$A^4$, $CR^1R^{1'}$–$CR^4R^{4'}$ and $NR^1$–$NR^4$ are saturated $sp^3$ carbon and nitrogen atoms respectively which are singly bonded to the adjacent ring atoms, except that when $R^1/R^{1'}$, $^{R2}/R^{2'}$, $R^3/R^{3'}$, and $R^4/R^{4'}$ represent a doubly bonded substituent exo to the ring (e.g., such as =O or an alkylene side chain), $CR^1R^{1'}$–$CR^4R^{4'}$ may also represent an $sp^2$ carbon atom. It will be further understood that, with respect to $A^1$–$A^4$, $CR^1$–$CR^4$ and N represent an unsaturated $sp^2$ carbon or nitrogen atom, which may be connected by an endocyclic double bond to an adjacent atom in the ring, provided such arrangement results in the creation of a stable compound.

 as used herein indicates a nitrogen heterocycle, which may be a saturated or unsaturated stable five-, six- or seven-membered monocyclic ring, or a seven- to ten-membered bicyclic ring containing up to three nitrogen atoms or containing one nitrogen atom and a heteroatom chosen from oxygen and sulfur, and which may be substituted on any atom that results in a stable structure. The nitrogen atom in such ring may be substituted so as to result in a quaternary nitrogen. The nitrogen heterocycle may be substituted in any stable position by $R^{20}$, for instance H, $C_{1-4}$alkoxy, F, Cl, Br, I, $NO_2$, $NR'_2$, OH, $CO_2R'$, $CONHR'$, $CF_3$, Q—$C_{0-4}$alkyl, Q—$C_{1-4}$alkyl—$S(O)_u$ (e.g., where u is 0, 1 or 2) or $C_{1-4}$alkyl substituted by any of the aforementioned sustituents. Representative of  are pyrroline, pyrrolidine, imidazole, imidazoline, imidazolidine, pyrazole, pyrazoline, pyrazolidine, piperidine, piperazine, morpholine, pyridine, pyridinium, tetrahydropyridine, tetrahydro- and hexahydro-azepine, quinuclidine, quinuclidinium, quinoline, isoquinoline, and tetra- and perhydro-quinoline and isoquinoline. In particular,  may be pyridyl, pyrolidinyl, piperidinyl, piperazinyl, azetidinyl, quinuclidinyl or tetrahydropyridinyl.  is preferably 4-pyridyl, 4-(2-amino-pyridyl), 4-tetrahydropyridyl, 4-piperidinyl or 4-piperazinyl.

C(O) indicates a carbon doubly bonded to oxygen (e.g., carbonyl), C(S) indicates a carbon doubly bonded to sulfur (e.g., thiocarbonyl).

t-Bu refers to the tertiary butyl radical, Boc refers to the t-butyloxycarbonyl radical, Fmoc refers to the fluorenyl-methoxycarbonyl radical, Ph refers to the phenyl radical, Cbz refers to the benzyloxycarbonyl radical, BrZ refers to the o-bromobenzyloxycarbonyl radical, ClZ refers to the o-chlorobenzyloxycarbonyl radical, Bzl refers to the benzyl radical, 4-MBzl refers to the 4-methyl benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. Tet refers to 5-tetrazolyl.

DCC refers to dicyclohexylcarbodiimide, DMAP refers to dimethylaminopyridine, DIEA refers to diisopropylethylamine, EDC refers to N-ethyl-N' (dimethylaminopropyl)carbodiimide. HOBt refers to 1-hydroxybenzotriazole, THF refers to tetrahydrofuran, DIEA refers to diisopropylethylamine, DMF refers to dimethylformamide, NBS refers to N-bromo-succinimide, Pd/C refers to a palladium on carbon catalyst, PPA refers to 1-propanephosphonic acid cyclic anhydride, DPPA refers to diphenylphosphoryl azide, BOP refers to benzotriazol-1-yloxy-tris(dimethylamino)phosphonium hexafluorophosphate, HF refers to hydrofluoric acid, TEA refers to triethylamine, TFA refers to trifluoroacetic acid, PCC refers to pyridinium chlorochromate.

The compounds of formula (I) are generally prepared by reacting a compound of the formula (V) with a compound of the formula (VI):

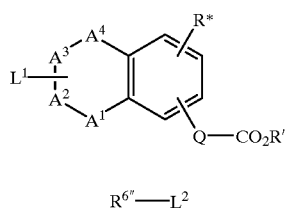

wherein
$A^{1-A4}$, R, R* and R' are as defined in formula (I), with any reactive functional groups protected;
$L^1$ and $L^2$ are functional groups which are capable of reacting to form the linkage —$(CR'R^{10})_r$—U—$(CR'_2)_s$—V—; and
$R^{6"}$ is W—$(CR'_2)_q$—Z— and any portion of the group —$(CR'R^7)_r$—U—$(CR'_2)_s$—V — which is connected to $L^2$, with any reactive functional groups protected;
and thereafter removing any protecting groups, and optionally forming a pharmaceutically acceptable salt.

It will be apparent that the precise identity of $L^1$ and $L^2$ will be dependent upon the site of the linkage being formed. General methods for preparing the linkage —$(CR'R^7)_r$—U—$(CR'_2)_s$—V— are described, for example, in EP-A 0 372 486 and EP-A 0 381 033 and EP-A 0 478 363, which are incorporated herein by reference.

For instance, if V is CONH, $L_1$ may be —$NH_2$, $L^2$ may be OH (as in an acid) or Cl (as in an acid chloride), and $R^{6"}$ may be W—$(CR'_2)_q$—Z—$(CR'R^{10})_r$—U—$(CR'_{2s}$—C(O), with any functional groups optionally protected. For example, $R^{6"}$ may be (benzyloxycarbonyl-amidino)benzoyl- or ($N^\alpha$-Boc,$N^{guan}$-Tos)arginyl-. When $L^2$ is OH, a coupling agent is used.

Similarly, if V is NHCO, $L^1$ may be —$CO_2H$ or CO—Cl, $L^2$ may be —$NH_2$, and $R^{6"}$ may be W—$(CR'_2)_q$—Z—$(CR'R^{10})_r$—U—$(CR'_2)_s$—. For example, $R^{6"}$ may be (benzyloxycarbonyl-amidino)phenyl, (benzyloxycarbonyl-amino)methylbenzyl- or 6-(benzyloxycarbonylamino) hexyl-.

Where V is $NHSO_2$, $L^1$ may be $SO_2Cl$, $L^2$ may be —$NH_2$ and $R^{6"}$ may be as above. Where V is $SO_2NH$, $L^1$ may be —$NH_2$ and $L^2$ may be $SO_2Cl$. Methods to prepare such sulfonyl chlorides are disclosed, for instance, in *J. Org. Chem.*, 23, 1257 (1958).

If V is CH=CH, $L^1$ may be —CHO, $L^2$ may be CH=P—$Ph_3$ and $R^{6"}$ may be W—$(CR'_2)_q$—Z—$(CR'R^{10})_r$—U—$(CR'_2)_s$—. Alternately, $L^1$ may be CH=P—$P_3$, $L^2$ may be CHO, e.g., $R^{6"}$ may be W—$(CR'_2)_q$—Z—$(CR'R^{10})_r$—U—$(CR'_2)_{s-1}$—CHO.

Where V is $CH_2CH_2$ may be obtained by reduction of a suitably protected compound wherein V is CH=CH.

Where V is $CH_2O$, $CH_2N$ or $C{\equiv}C$, $L^1$ may be —OH, —NH or $-C{\equiv}CH$, respectively; $L^2$ may be —Br; and $R^{6"}$ may be W—$(CR'_2)_q$—Z—$(CR'R^{10})_r$—U—$(CR'_2)_s$—. For example, $R^{6"}$ may be (benzyloxycarbonylamino)-methylbenzyl- or 2-(N-benzyl-4-piperidinyl)-ethyl. Similarly where U or V is $OCH_2$, $NR'CH_2$ or, $L^1$ may be —$CH_2Br$ and $L^2$ may be —OH, —NH or —H, respectively. Alternately, when U or V is $C{\equiv}C$, $L^1$ may be Br, I or $CF_3SO_3$, $L^2$ may be $C{\equiv}CH$ and the coupling may be catalyzed by palladium and a base.

Compounds wherein V is $CHOHCH_2$ may be prepared from a suitably protected compound where V is CH=CH by the procedure disclosed in *J. Org. Chem.*, 54, 1354 (1989).

Compounds wherein V is CH2CHOH may be obtained from a suitably protected compound where V is CH=CH by hydroboration and basic oxidation as disclosed in *Tet. Lett.*, 31, 231 (1990).

Compounds of formula (I) are prepared by the general methods described in Schemes I–IV.

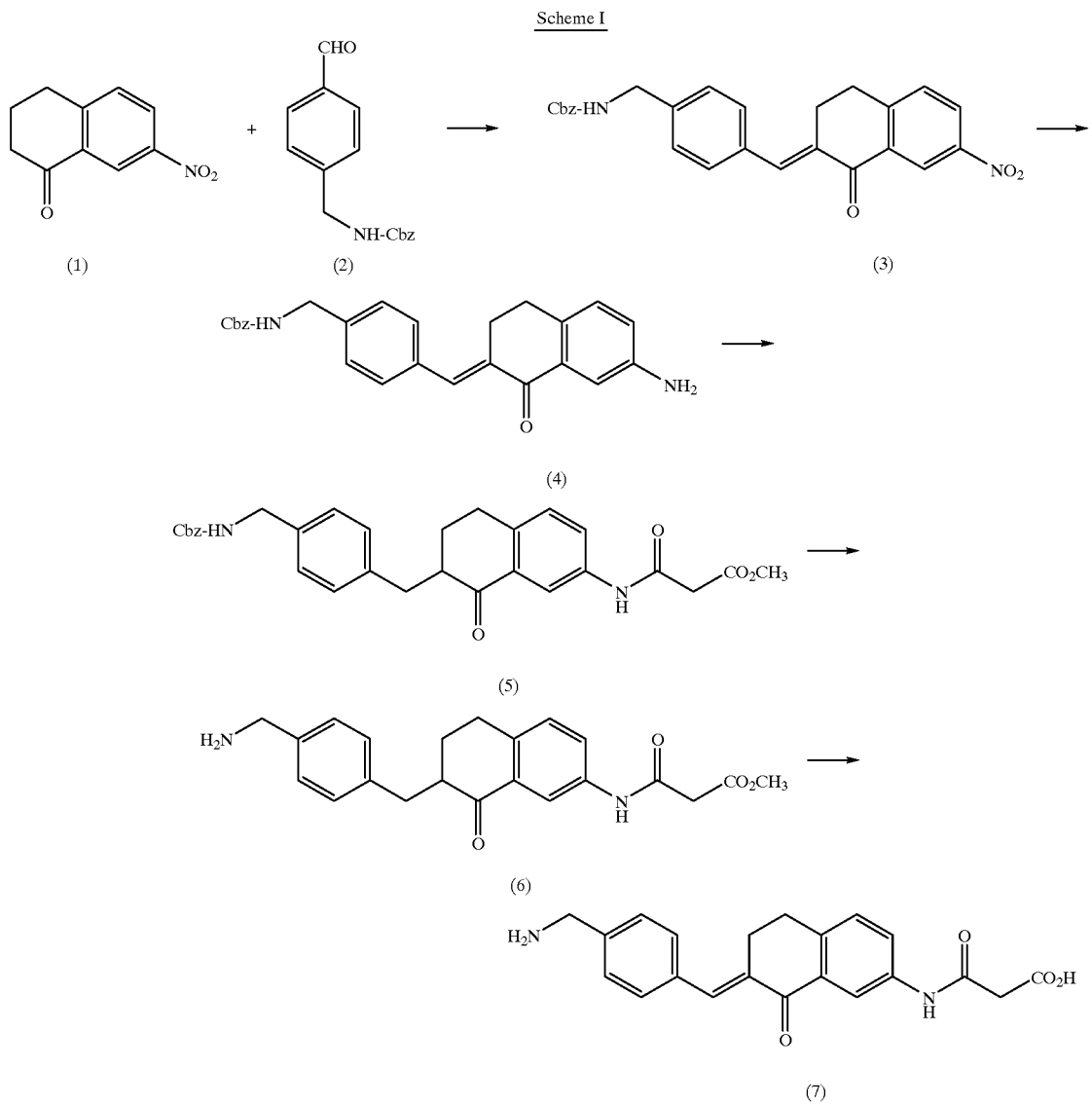

Scheme I

Scheme I shows the synthesis of formula (I) compounds wherein $A^1$ is C=O, $A^2$ is $CHR^6$, $A^3$ is $CH_2$, and $A^4$ is $CH_2$. Generally, the synthesis is begun with a substituted tetralone, wherein the substituents on said tetralone are dependent upon the linkers —Q— and —$(CR'R^7)_r$—U—$(CR'_2)_s$—V— in the targeted formula (I) compound. According to Scheme I, acid-catalyzed olefination, for example, using sulfuric acid in glacial acetic acid, of a formula (1) nitrotetralone compound with an aldehyde of formula (2) results in the formation of a formula (3) tetralone compound, which is a precussor to formula (I) compounds wherein Q is —NHC(O)$CH_2$— and —$(CR'R^7)_r$—U—$(CR'_2)_s$—V— is —$CH_2$—. Reduction of the formula (3) nitro group, for example, using iron in the presence of acid, such as glacial acetic acid, provides the formula (4) amine compound. Acylation of this amine with, for example, methyl malonyl chloride, in the presence of a base, such as triethylamine, in a suitable solvent, such as methylene chloride, yields a formula (5) compound. Concomitant reduction of the olefin and removal of the Cbz-group on the amine of the formula (5) compound, using for example, hydrogen in the presence of a catalyst, such as palladium on carbon, in a suitable solvent, such as in methanol, results in the formation of the formula (6) amine,ester compound, which is also a formula (I) compound. This amine ester may be used to prepare additional formula (I) compounds by saponifying the ester group using base, for example, sodium hydroxide, in a suitable solvent system, such as water/methanol, to give the carboxy formula (7) compound. It should be appreciated by those skilled in the art that the Scheme I, formula (2) compound is representative of a formula (VI), $R^{6"}$—$L^2$, compound and the selection of an appropriately substituted aldehyde would result in the formation of formula (I) compounds bearing the various $R^6$ substituents.

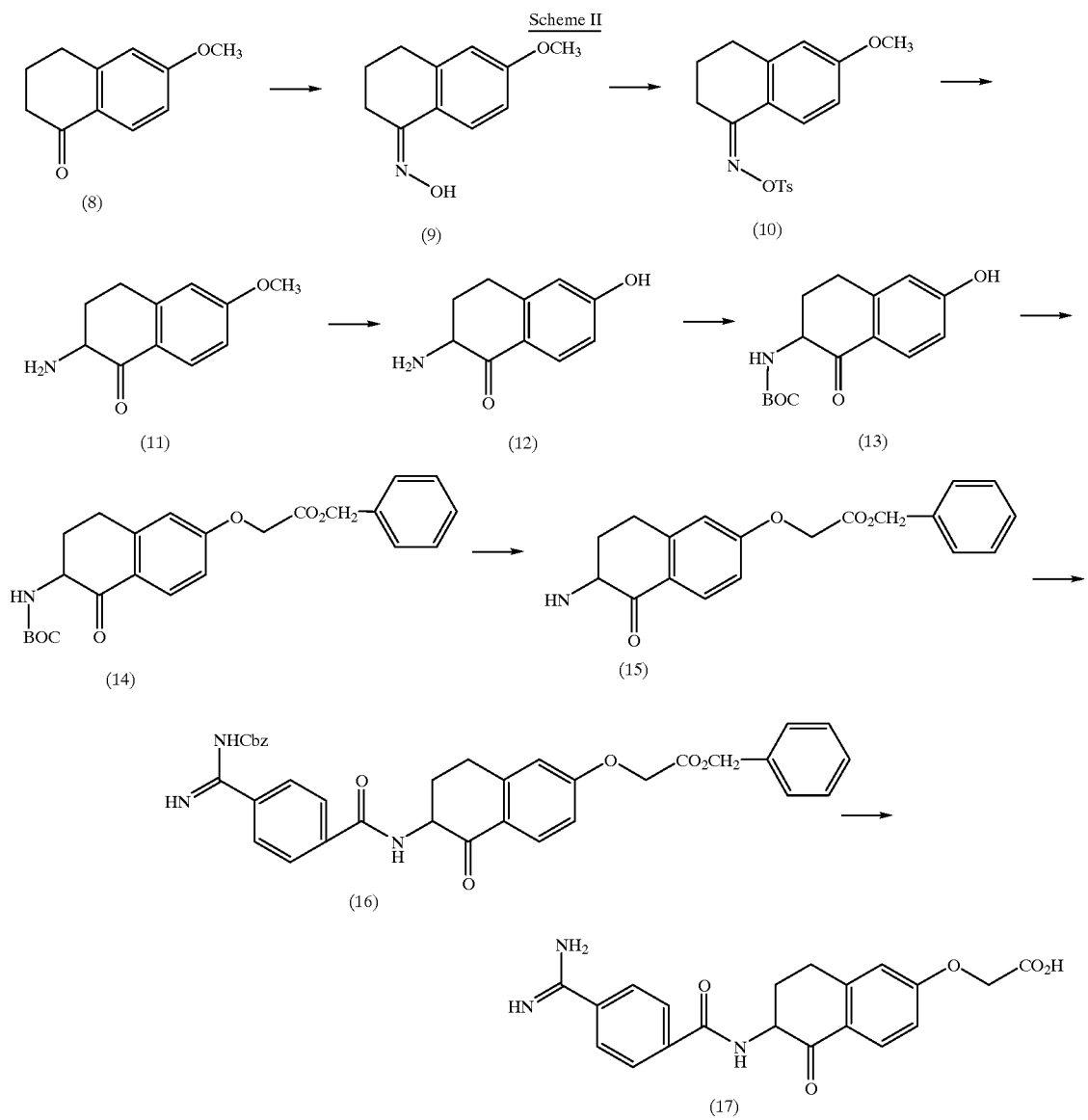

Scheme II shows an alternate synthesis for the preparation of formula (I) compounds wherein $A^1$ is C=O, $A^2$ is $CHR^6$, $A^3$ is $CH_2$, and $A^4$ is $CH_2$. Again, the synthesis is begun with an appropriately substituted tetralone, which is commercially available or is synthesized by known procedures. According to Scheme II, the ketone functionality of a formula (8) compound is converted to the corresponding oxime derivative using hydroxylamine. The hydroxy portion of the formula (9) hydroxylamine compound is then protected, for example, as a sulfonate ester, such as a p-toluenesulfonate (Ts) derivative. The formula (11) aminotetralone compound is then prepared by reacting the formula (10) compound with, for example, potassium ethoxide. Conversion to the hydroxy compound of formula (12) is accomplished by employing an ether-cleaving reagent, for example, refluxing hydrobromic acid. The amino group is then protected as the Boc derivative using di-tert-butyl dicarbonate. The hydroxy group of the formula (13) compound is alkylated using, for example, benzyl 2-bromacetate, in the presence of a base, such as potassium carbonate, in a suitable solvent, such as acetone, to give a formula (14) compound. Removal of the Boc protecting group is accomplished using conventional techniques, for example, by reacting the formula (14) compound with acid, such as hydrochloric acid. The amino group of the formula (15) compound is then acylated/coupled with a suitably protected carboxylic acid, $R^{6''}$—OH, which according to Scheme II is a 4-(Cbz-aminoiminomethyl)benzoic acid. The condensation of the amino group with the $R^{6''}$—OH, wherein $R^{6''}$ is as defined in formula (VI), is carried out in the presence of an amide-forming agent, such as N-ethyl-N'-(dimethylaminopropyl)carbodiimide, in the presence of 1-hydroxybenzotriazole, and a base, such as diisopropylethyl amine, in a suitable solvent, such as dimethylformamide. Protecting groups, such as those for amino or carboxy, are selectively removed by methods known in the art. For example, a Cbz-group on a nitrogen atom and a benzyl group on a carboxylic acid moiety may be removed by hydrogenation in the presence of a catalyst, such as palladium on carbon, in an acidic medium such as in glacial acetic acid to give a formula (17) compound, which is also a formula (I) compound.

Scheme III

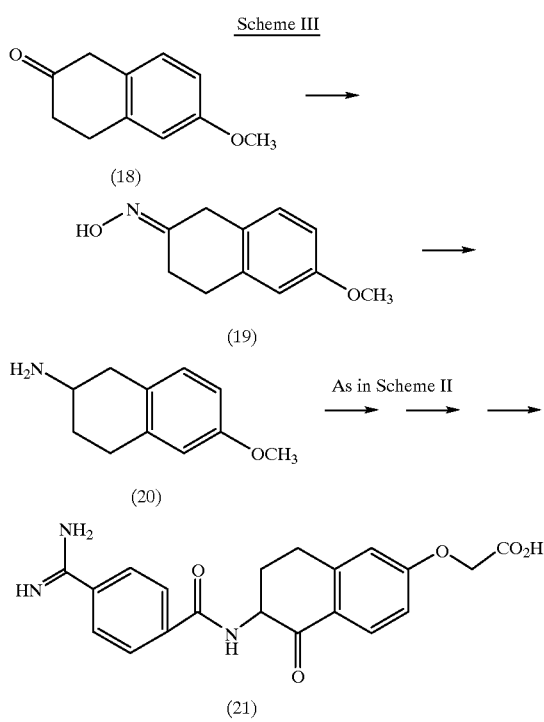

Scheme III shows the synthesis of formula (I) compounds wherein $A^1$, $A^2$ and $A^4$ are $CH_2$ and $A^3$ is $CHR^6$. According to Scheme III, a methoxy-substituted dihydronaphthalene-2 (1H)-one of formula (18) is the starting point for the synthesis of 1,2,3,4-tetrahydronaphthalenone compounds represented by the formula (21) compound. The ketone functionality of the formula (18) compound is converted to the oxime derivative using hydroxylamine. Reduction of the oxime to the corresponding amine compound of formula (20) is accomplished, for example, by hydrogenation, in the presence of a catalyst, such as palladium on carbon, in a suitable solvent system, such as hydrochloric acid/methanol. The formula (21) compound is prepared from the formula (20) methoxy,amino compound following the steps detailed in Scheme (II), formulae (11)–(17).

The compounds of formula (V), wherein one of $A^2$ or $A^3$ is nitrogen, are tetrahydroisoquinolines and are prepared by the general methods illustrated by Scheme IV. Representative methods for preparing tetrahydroisoquinolines are well known in the art (e.g., Kametani and FuKumoto, Isoquinolines, ed. G. Grethe, Wiley-Interscience, New York, 1981, p. 139 and Gilchrist, *Heterocyclic Chemistry*, Pitman Publishing, London, 1985, p.272).

Scheme IV

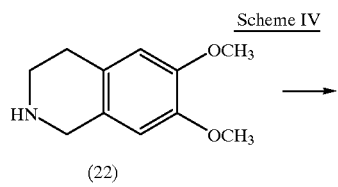

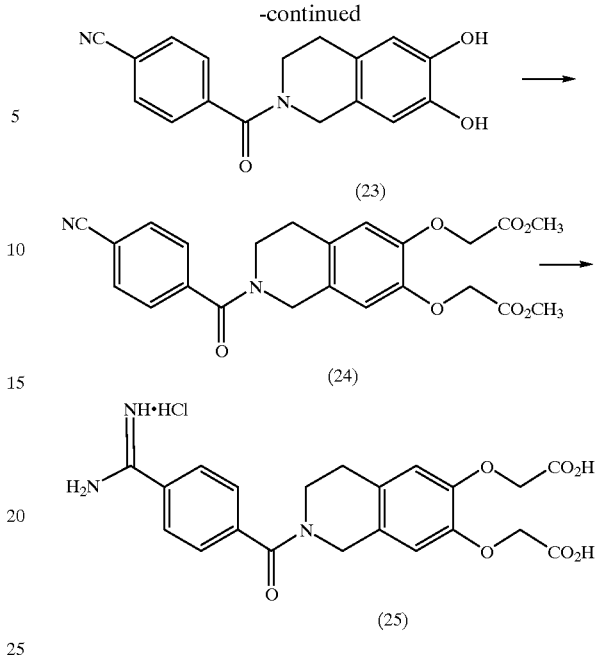

Scheme IV shows the synthesis of formula (I) compounds wherein $A^1$, $A^3$, and $A^4$ are $CH_2$ and $A^2$ is $NR^6$. According to Scheme IV, the dimethoxy-substituted tetrahydroisoquinoline of formula (22) is the starting point for the synthesis of the formula (I) 1,2,3,4-tetrahydroisoquinoline compounds of formula (25). In this synthesis the dimethoxy compound is converted to its corresponding dihydroxy derivative using an ether-cheaving reagent, such as 48% hydrobromic acid. The amine functionality of this tetrahydroisoquinoline intermediate is then acylated under standard amide-forming conditions, for example, in a reaction with a N-hydroxysuccinimide (NHS) ester of a carboxylic acid, such as the NHS-ester of 4-cyanobenzoic acid, in the presence of a coupling reagent, such as dicyclohexylcarbodiimide, and a base, such as triethylamine, to give the formula (23) compound. Alkylation of the free hydroxy groups of the formula (23) compound using, for example, methyl bromoacetate in the presence of a base, such as potassium carbonate, yields the formula (24) compound. Conversion of the nitrile of the formula (24) compound to the amidine derivative is accomplished by reacting the nitrite with hydroxchloric acid, followed by reaction with ammonium acetate. The ester protecting groups can then by hydrolyzed to the corresponding free carboxylic acids using conventional techniques, for example, refluxing aqueous acetic acid, to give the formula (25) compound.

Coupling reagents as used herein denote reagents which may be used to form peptide bonds. Typical coupling methods employ carbodiimides, activated anhydrides and esters and acyl halides. Reagents such as EDC, DCC, DPPA, PPA, BOP reagent, HOBt, N-hydroxysuccinimide and oxalyl chloride are typical.

Coupling methods to form peptide bonds are generally well known to the art. The methods of peptide synthesis generally set forth by Bodansky et al., THE PRACTICE OF PEPTIDE SYNTHESIS, Springer-Verlag, Berlin, 1984, Ali et al. in *J. Med. Chem.*, 29, 984 (1986) and *J. Med. Chem.*, 30, 2291 (1987) are generally illustrative of the technique and are incorporated herein by reference.

Solution synthesis for the formation of amide or peptide bonds is accomplished using conventional methods used to form amide bonds. Typically, the amine or aniline is coupled via its free amino group to an appropriate carboxylic acid substrate using a suitable carbodiimide coupling agent, such as N,N'-dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran(THF), in the presence of a base, such as N-methyl morpholine, DMAP or a trialkylamine, with isobutyl chloroformate to form the "activated anhydride", which is subsequently reacted with the free amine of a second protected amino acid or aniline.

Compounds of formula (VI) are prepared by conventional methods known in the art from commercially available materials. W is a generally a basic functional group attached to Z, optionally via an alkyl chain, and is protected during the synthesis of $R^6$ or is introduced into the molecule after the $-(CR'R^7)_r-U-(CR'_2)_s-V-$ linkage has been formed. For example, compounds of formula (I) wherein W is a suitably substituted R'R"N—, R"R'NC(=NR'), R'$_2$N(R$^8$)C=N—, R"N=(R$^8$)C—NR'—, R'$_2$N(R'$_2$N)C=N— or R"R'N(R'N=)C—NR', are prepared by conventional methods including those disclosed in EP-A 0 372 486, EP-A 0 381 033 or EP-A 0 478 363, which are incorporated herein by reference.

Compounds of formula (VI) wherein W is Ⓝ are prepared, inter alia, by methods disclosed in EP-A 0 478 363.

Compounds wherein W is R'$_2$N(R'$_2$N)C=N—X— or R"R'N(R'N=)C—NR'—X—, and X is O are prepared, inter alia, by methods disclosed in *J. Org. Chem.*, 51, 5047 (1986).

Compounds wherein W is R'$_2$N(R'$_2$N)C=N—X— or R"R'N(R'N=)C—NR'—X—, and X is N=CR', are prepared, inter alia, by methods disclosed in U.S. Pat. No. 3,714,253 and *Eur. J. Med. Chem.-Chim. Ther.*, 20, 25 (1985).

Compounds wherein W is R'$_2$N(R'$_2$N)C=N—X— or R"R'N(R'N=)C—NR'—X—, and X is C(O), are prepared, inter alia, by methods disclosed in U.S. Pat. No. 3,714,253 and *Can. J. Chem.*, 43, 3103 (1965).

Compounds wherein W is R'ONR'C(=NR')— may be prepared, inter alia, by methods disclosed in *J. Het. Chem.*, 16, 1063 (1979) or *J. Het. Chem.*, 26, 125 (1989).

Compounds wherein W is R'$_2$NR'NC(=NR')— are prepared by conventional methods including those disclosed in Syn., 583 (1974).

Compounds wherein W is R'R"NR'N=— are prepared, inter alia, by methods disclosed in *J. Prakt. Chem.*, 36, 29 (1967).

Compounds wherein W is R'R"NR'NCO— are prepared, inter alia, by methods disclosed in *Bull. Chem. Soc. Jpn.*, 43, 2257 (1970).

Compounds wherein W is R"R'NC(=NR')Y, and Y is S, are prepared, inter alia, by methods disclosed in *Chem. Lett.*, 1379 (1986).

Compounds of formula (VI) or formula (I), wherein W is R"R'NC(=NR')Y and Y is O, are prepared by conventional methods including those disclosed in Japanese Patent 2022751.

Useful intermediates of formula (VI) include compounds of the formula W'—(CR'$_2$)$_q$—Z—(CR'R$^{10}$)$_r$—U—(CR'$_2$)$_s$—L$^2$, wherein Z, R', R", R$^{10}$, U, q, r, and s are as defined for formula (I); L$^2$ is CHO, CO$_2$R', OH, Cl, Br, I, CH2—T or NR'R", and T is CF$_3$SO$_3$, OH, NHR", Cl, Br or I; and W' is W with any reactive basic nitrogen group protected as herein described. R'SO$_2$, R'OCO and R'CO (e.g., Tos, Boc, Cbz or acetyl) are typical nitrogen protecting groups. Particular examples of such intermediates are:

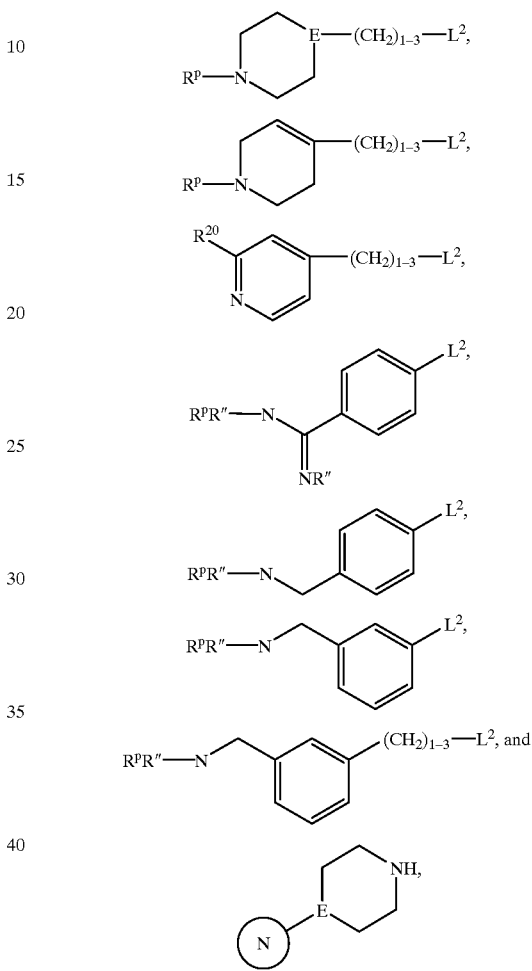

wherein E is N or CH, R$^{20}$ is hydrogen, amino, mono or di-C$_{1-4}$alkylamino, hydroxy or C$_{1-4}$alkyl.

The reactive functional groups of the sidechains of each synthetic fragment are suitably protected as known in the art. Suitable protective groups are disclosed in Greene, PROTECTIVE GROUPS IN ORGANIC CHEMISTRY, John Wiley and Sons, New York, 1981. For example, the Boc, Cbz, phthaloyl or Fmoc group may be used for protection of an amino or amidino group. The Boc group is generally preferred for protection of an α-amino group. A t-Bu, cHex or benzyl ester may be used for the protection of the side chain carboxyl. A benzyl group or suitably substituted benzyl group (e.g., 4-methoxy-benzyl or 2,4-dimethoxy-benzyl) is used to protect the mercapto group or the hydroxyl group. The tosyl group may be used for protection of the imidazolyl group and tosyl or nitro group for protection of the guanidino group. A suitably substituted carbobenzyloxy group or benzyl group may be also be used for the hydroxyl group or amino group. Suitable substitution of the carbobenzyloxy or benzyl protecting groups is ortho and/or para substitution with chloro, bromo, nitro or methyl, and is used to modify the reactivity of the protective group. Except for the Boc group, the protective groups for the amino moiety are, most conveniently, those which are not removed by mild acid treatment. These protective groups are removed by such methods as catalytic hydrogenation, sodium in liquid ammonia or HF treatment, as known in the art.

Modification of amino groups especially on the six-membered ring of the bicyclic system, may be accomplished by alkylation, sulfonylation, cyanation or acylation as is generally known in the art.

Acid addition salts of the compounds of this invention are prepared in a standard manner in a suitable solvent from the parent compound and an excess of an acid, such as hydrochloric, hydrobromic, sulfuric, phosphoric, acetic, maleic, succinic or methanesulfonic. The acetate salt form is especially useful. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li+, Na+, K+, Ca++, Mg++ and $NH_4$+ are specific examples of cations present in pharmaceutically acceptable salts.

This invention provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, the compounds of this invention may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds of this invention may be used in vitro to inhibit the aggregation of platelets in blood and blood products, e.g., for storage, or for ex vivo manipulations such as in diagnostic or research use.

This invention also provides a method of inhibiting platelet aggregation and clot formation in a mammal, especially a human, which comprises the internal administration of a compound of formula (I) and a pharmaceutically acceptable carrier. Indications for such therapy include acute myocardial infarction (AMI), deep vein thrombosis, pulmonary embolism, dissecting anurysm, transient ischemia attack (TIA), stroke and other infarct-related disorders, and unstable angina. Chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TTP), snake venom and immune diseases, are likely to be responsive to such treatment. In addition, the compounds of this invention may be useful in a method for the prevention of metastatic conditions, the prevention or treatment of fungal or bacterial infection, inducing immunostimulation, treatment of sickle cell disease, and the prevention or treatment of diseases in which bone resorption is a factor.

The compounds of formula (I) are administered either orally or parenterally to the patient, in a manner such that the concentration of drug in the plasma is sufficient to inhibit platelet aggregation, or other such indication. The pharmaceutical composition containing the compound is administered at a dose between about 0.2 to about 50 mg/kg in a manner consistent with the condition of the patient. For acute therapy, parenteral administration is preferred. For persistent states of hyperaggregability, an intravenous infusion of the peptide in 5% dextrose in water or normal saline is most effective, although an intramuscular bolus injection may be sufficient.

For chronic, but noncritical, states of platelet aggregability, oral administration of a capsule or tablet, or a bolus intramuscular injection is suitable. The compound of this invention is administered one to four times daily at a level of about 0.4 to about 50 mg/kg to achieve a total daily dose of about 0.4 to about 200 mg/kg/day.

This invention further provides a method for inhibiting the reocclusion of an artery or vein following fibrinolytic therapy, which comprises internal administration of a compound of formula (I) and a fibrinolytic agent. It has been found that administration of an peptide in fibrinolytic therapy either prevents reocclusion completely or prolongs the time to reocclusion.

When used in the context of this invention the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants, thereof, which retain plasminogen activator activity, such as variants which have been chemically modified or in which one or more amino acids have been added, deleted or substituted or in which one or more or functional domains have been added, deleted or altered such as by combining the active site of one plasminogen activator with the fibrin binding domain of another plasminogen activator or fibrin binding molecule. Other illustrative variants include tPA molecules in which one or more glycosylation sites have been altered. Preferred among plasminogen activators are variants of tPA in which the primary amino acid sequence has been altered in the growth factor domain so as to increase the serum half-life of the plasminogen activator. tPA Growth factor variants are disclosed, e.g., by Robinson et al., EP-A 0 297 589 and Browne et al., EP-A 0 240 334. Other variants include hybrid proteins, such as those disclosed in EP 0 028 489, EP 0 155 387 and EP 0 297 882, all of which are incorporated herein by reference. Anistreplase is a preferred hybrid protein for use in this invention. Fibrinolytic agents may be isolated from natural sources, but are commonly produced by traditional methods of genetic engineering.

Useful formulations of tPA, SK, UK and pUK are disclosed, for example, in EP-A 0 211 592, EP-A 0 092 182 and U.S. Pat. No. 4,568,543, all of which are incorporated herein by reference. Typically the fibrinolytic agent may be formulated in an aqueous, buffered, isotonic solution, such as sodium or ammonium acetate or adipate buffered at pH 3.5 to 5.5. Additional excipients such as polyvinyl pyrrolidone, gelatin, hydroxy cellulose, acacia, polyethylene, glycol, mannitol and sodium chloride may also be added. Such a composition can be lyophilized.

The pharmaceutical composition may be formulated with both the compound of formula (I) and fibrinolytic in the same container, but formulation in different containers is preferred. When both agents are provided in solution form they can be contained in an infusion/injection system for simultaneous administration or in a tandem arrangement.

Indications for such therapy include myocardial infarction, deep vein thrombosis, pulmonary embolism, stroke and other infarct-related disorders. The compound of formula (I) is administered just prior to, at the same time as, or just after parenteral administration of tPA or other fibrinolytic agent. It may prove desirable to continue treatment with the peptide for a period of time well after reperfusion has been established to maximally inhibit post-therapy reocclusion. The effective dose of tPA, SK, UK or pUK may be from 0.5 to 5 mg/kg and the effective dose of the compound of this invention may be from about 0.1 to 25 mg/kg.

For convenient administration of the inhibitor and the fibrinolytic agent at the same or different times, a kit is prepared, comprising, in a single container, such as a box, carton or other container, individual bottles, bags, vials or other containers each having an effective amount of the inhibitor for parenteral administration, as described above, and an effective amount of tPA, or other fibrinolytic agent, for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the fibrinolytic and the compound of this invention may be packaged separately, as in two containers, or lyophilized together as a powder and provided in a single container.

When both agents are provided in solution form, they can be contained in an infusion/injection system for simultaneous administration or in a tandem arrangement. For example, the platelet aggregation inhibitor may be in an i.v. injectable form, or infusion bag linked in series, via tubing, to the fibrinolytic agent in a second infusion bag. Using such a system, a patient can receive an initial bolus-type injection or infusion, of the peptide inhibitor followed by an infusion of the fibrinolytic agent.

The pharmacological activity of the compounds of this invention is assessed by their ability to inhibit the binding of $^3$H-SK&F 107260, a known RGD-fibrinogen antagonist, to the GPIIbIIIa receptor; their ability to inhibit platelet aggregation, in vitro, and their ability to inhibit thrombus formation in vivo.

Inhibition of RGD-Mediated GPIIb-IIIa Binding
Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mM CaCl$_2$ at 4° C. for 2 h. The lysate was centrifuged at 100,000 g for 1 h. The supernatant obtained was applied to a 5 mL lentil lectin sepharose 4B column (E.Y. Labs) preequilibrated with 20 mM Tris-HCl, pH 7.4, 100 mM NaCl, 2 mM CaCl$_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.
Incorporation of GPIIb-IIIa in Liposomes.

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM CaCl2 (with 2 changes). The GPIIb-IIIa-containing liposomes wee centrifuged at 12,000 g for 15 min and resuspended in the dialysis buffer at a final protein concentration of approximately 1 mg/mL. The liposomes were stored at −70 C. until needed.
Competitive Binding to GPIIb-IIIa The binding to the fibrinogen receptor (GPIIb-IIIa) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 μg/mL polylysine (Sigma Chemical Co., St. Louis, Mo.) at room temperature for 1 h to block nonspecific binding. Various concentrations of unlabeled benzadiazapines were added to the wells in quadruplicate. [$^3$H]-SK&F-107260 was applied to each well at a final concentration of 4.5 nM, followed by the addition of 1 μg of the purified platelet GPIIb-IIIa-containing liposomes. The mixtures were incubated for 1 h at room temperature. The GPIIb-IIIa-bound [3H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 μM unlabeled SK&F-107260 and was consistently less than 0.14% of the total radioactivity added to the samples. All data points are the mean of quadruplicate determinations.

Competition binding data were analyzed by a nonlinear least-squares curve fitting procedure. This method provides the IC50 of the antagonists (concentration of the antagonist which inhibits specific binding of [$^3$H]-SK&F-107260 by 50% at equilibrium). The IC50 is related to the equilibrium dissociation constant (Ki) of the antagonist based on the Cheng and Prusoff equation: Ki =IC50/(1+L/Kd), where L is the concentration of [3H]-SK&F-107260 used in the competitive binding assay (4.5 nM), and Kd is the dissociation constant of [3H]-SK&F-107260 which is 4.5 nM as determined by Scatchard analysis. The compounds of this invention inhibit [3H]-SK&F 107260 binding with Ki in the range of about 20 µM to about 200 µM.

Inhibition of Platelet Aggregation

Blood was collected (citrated to prevent coagulation) from, naive, adult mongrel dogs. Platelet rich plasma, PRP, was prepared by centrifugation at 150×g for 10 min at room temperature. Washed platelets were prepared by centrifuging PRP at 800×g for 10 min. The cell pellet thus obtained was washed twice in Tyrode's buffer (pH 6.5) without Ca++ and resuspended in Tyrode's buffer (pH 7.4) containing 1.8 mM Ca++ at 3×10$^5$ cells/ml. Peptides were added 3 min prior to the agonist in all assays of platelet aggregation. Final agonist concentrations were 0.1 unit/ml thrombin and 2 mM ADP (Sigma). Aggregation was monitored in a Chrono-Log Lumi-Aggregometer. Light transmittance 5 min after addition of the agonist was used to calculate percent aggregation according to the formula % aggregation =[(90−CR)÷(90−10)×100, where CR is the chart reading, 90 is the baseline, and 10 is the PRP blank reading. IC50's were determined by plotting [% inhibition of aggregation] vs. [concentration of peptide]. Peptides were assayed at 200 mM and diluted sequentially by a factor of 2 to establish a suitable dose response curve. The compounds of this invention inhibit the aggregation of human platelets stimulated with ADP with IC50 of about 10 to about 50 µM.

To assess the stability of the compounds to plasma proteases, the compounds were incubated for 3 h (rather than 3 min) in the PRP prior to addition of the agonist.

In Vivo Inhibition of Platelet Aggregation

In vivo inhibition of thrombus formation is demonstrated by recording the systemic and hemodynamic effects of infusion of the peptides into anesthetized dogs according to the methods described in Aiken et al., *Prostaglandins*, 19, 629 (1980).

The examples which follow are intended to in no way limit the scope of this invention, but are provided to illustrate how to make and use the compounds of this invention. Many other embodiments will be readily apparent and available to those skilled in the art.

EXAMPLE 1

2-(4-Aminomethyl)benzyl-7-amidomalonyl-1-tetralone a) 7-Nitrotetralone (2.3208 g, 12.14 mmol) was dissolved in glacial acetic acid. The Cbz derivative of 4-formylbenzylamine (5.0 g, 18.57 mmol) was added, followed by 5 mL of concentrated sulfuric acid. The reaction was left stirring overnight at room temperature. The reaction was quenched with water and extracted with ethyl acetate (2×). The organic phase was carefully neutralized with excess aqueous sodium bicarbonate. The ethyl acetate was separated, dried over anhydrous magnesium sulfate, filtered and evaporated under vacuum. The residue was triturated with hexanes:ethyl acetate (7:3, 100 mL). After sonication, the precipitated material was collected by filtration (3.41 g, 63%).

b) The product from Example 1(a) (5.25, 1.19 mmol) was dissolved in ethanol. Iron (0.54 g) was added, followed by glacial acetic acid (5.0 mL). The reaction was heated to reflux. After 2 hours, the reaction was allowed to cool to room temperature and evaporated under vacuum. The residue was taken up in chloroform and flash chromatographed on silica gel (4.54 g, 93%).

c) The amino tetralone from Example 1(b) (2.2 g, 0.53 mmol) was dissolved in methylene chloride. Methyl malonyl chloride (115 µl, 0.1464 g, 1.07 mmol) was added followed by triethylamine (150 µl, 0.1091 g, 1.07 mmol). The reaction was stirred at room temperature overnight. The reaction was evaporated under vacuum to yield 1.801 g of crude material. The isolated material was flash chromatographed on silica gel, eluting with 0.2% methanol in chloroform (66.5 mg).

d) The compound from Example 1(c) was dissolved in methanol. Palladium on carbon (10%) was then added. The reaction flask was fitted with a rubber septum and purged with hydrogen. A reservoir of hydrogen via a balloon fitted with a needle was placed on top of the flask, through a septum. After 1 hour, the reaction mixture was filtered through Celite® and the filtrate was evaporated under vacuum (99 mg).

e) 2-(4-Aminomethyl)benzyl-7-amidomalonyl-1-tetralone, methyl ester from Example 1(d) was dissolved in methanol. Aqueous sodium hydroxide (1.0N, 0.5 mL, 0.5 mmol) was added and the solution was stirred at room temperature overnight. After 24 hours, the reaction was slowly acidified with 1N aqueous hydrochloric acid. The solution was evaporated under vacuum, leaving a solid white residue. The residue was dried under vacuum. This residue was taken up in methanol, sonicated and the turbid solution filtered through a sintered glass funnel. This solution was chromatographed on Sephadex LH20, eluted with methanol. One fraction was collected. The residue was taken up in methanol and precipitated with diethyl ether. The mixture was left standing at room temperature to allow the compound to settle. The precipitate was collected on a sintered glass funnel and dried under vacuum to give 113.8 mg of 2-(4-aminomethyl)benzyl-7-amidomalonyl-1-tetralone. 400 MHz $^1$H NMR, (DMSO-d6): 8.14 ppm (s, 1H), 7.75 (d, 1H), 7.45 (d, 2H), 7.34–7.08 (m, 4H), 3.97 (s, 2H), 3.29 (dd, 2H), 3.24 (s, 2H), 2.95–2.76 (m, 3H), 2.72–2.61 (m, 2H), 2.04–2.87 (m, 2H), 2.76–2.58 (m, 2H). MS (ES) 376.0 (M+H)$^+$.

EXAMPLE 2

2-[[4-Aminoiminomethyl)benzoyl]amino]-6-acetyloxy-1-tetralone a) 6-Methoxy-1-tetralone oxime A solution of 6-methoxy-1-tetralone (40 g, 227 mmol), potassium carbonate (64 g, 462 mmol) and hydroxylamine-.hydrochloride (63.2 g, 909 mmol) in methanol (500 mL) and water (56 mL) was refluxed for 2.5 hours. The potassium carbonate was filtered off, poured into ice (300 g) and water was added to total 1.5 L. The precipitate was collected to give 34.79 g (80%) of crude product, which recrystallized in methanol to give 20.4 g (47%) of a white solid.

b) 6-Methoxy-1-tetralone oxime O-p-toluensulfonate

A solution of p-toluensulfonyl chloride (17.6 g, 92 mmol) in pyridine (80 mL) was added dropwise with stirring to an ice-cooled solution of 6-methoxy-1-tetralone oxime in pyridine (80 mL) under argon. After stirring in an ice bath for 0.5 hours and then at room temperature for 22 hours, the mixture was poured into ice-water (600 mL). The precipitate was collected and recrystallized in methylene chloride/petroleum ether to give 28.88 g (91%) of white crystals.

c) 2-Amino-6-methoxy-1-tetralone, hydrochloride

A solution of potassium ethoxide in absolute ethanol (30 mL) was added dropwise to a solution of 6-methoxy-1-tetralone oxime O-p-toluensulfonate in dry benzene (50 mL) at 0° C. over a 10 minute period under argon. After stirring for 1 hour, the reaction mixture was allowed to stand in a refrigerator overnight. The precipitate was removed by filtration through a coarse sintered glass funnel and washed with ether (100 mL) The filtrate was cooled in an ice-bath with stirring and concentrated hydrochloric acid (5 mL) was slowly added. The reaction mixture was concentrated. A small amount of methanol and methylene chloride were added and the liquid was decanted off. The resulting crude product was kept in the refrigerator for 24 hours to give a brownish-green liquid and a white precipitate. The solid was filtered off and the filtrate was concentrated. The crude product was subjected to re-evaporation in dry toluene and hexane gave 2.68 g (48%) of grey solid.

d) 2-Amino-6-hydroxy-1-tetralone, hydrobromide

A mixture of 2-amino-6-methoxy-1-tetralone hydrochloride (2 g, 8.79 mmol) and 48% hydrobromic acid (60 mL) was stirred at 100° C. for 2 hours and then increased to 130° C. for additional 100 minutes. The resulting solution was concentrated. The crude product was subjected to re-evaporation with dry toluene and hexane. Upon adding a small amount of ethanol and hexane, a white salt precipitated which was removed. Upon concentrating the filtrate, a purple solid (1.43 g, 63%) resulted.

e) N-t-BOC-2-amino-6-hydroxy-1-tetralone

A solution of di-tert-butyl dicarbonate (1.07 g, 4.91 mmol) in dioxane (20 mL) was added dropwise to a mixture containing 2-amino-6-hydroxy-1-tetralone hydrobromide (1.15 g, 4.46 mmol), 2N sodium hydroxide (10 mL), and dioxane (60 mL) at 0° C. over a 10 minute period. The reaction mixture was stirred at room temperature for 2.3 hours and then it was concentrated. Water (120 mL) was then added to the residue which was acidified to pH 6 using 1N sodium bisulfate. The mixture was extracted with ethyl acetate (3×100 mL) and the organic layer was washed with water (50 mL), brine (50 mL), and dried over sodium sulfate. After filtration, the filtrate was concentrated to give 0.92 g (75%) of a crude product. Silica gel chromatography (5% methanol/methylene chloride) gave the title compound (0.28 g, 23%)

f) N-t-BOC-2-amino-6-(benzyloxycarbonylmethoxy)-1-tetralone

A mixture of N-t-Boc-2-amino-6-hydroxy-1-tetralone (0.24 g, 0.87 mmol), potassium carbonate (0.13 g, 0.94 mmol), and acetone (18 mL) was refluxed under argon for 25 minutes. The reaction mixture was cooled down to room temperature before adding a solution of benzyl 2-bromoacetate (0.24 g, 0.1 mmol) in acetone (8 mL). The reaction mixture was stirred at reflux temperature overnight. The reaction mixture was filtered through a coarse sintered glass funnel and washed with acetone. The filtrate was concentrated in vacuo and re-dissolved in methylene chloride (60 mL), washed with water (10 mL), 5% sodium carbonate (10 mL) and dried over sodium sulfate. After filtration, the filtrate was concentrated to give 0.39 g of crude product. Silica gel chromotagraphy (1:4 ethyl acetate/hexane) gave the title compound (0.25 g, 67%) as a white solid.

g) 2-Amino-6-(benzyloxycarbonylmethoxy)-1-tetralone, hydrochloride

To a solution of 4N hydrochloric acid/dioxane (20 mL), N-t-Boc-2-amino-6-(benzyloxycarbonylmethoxy)-1-tetralone (0.24 g, 0.55 mmol) was stirred at room temperature for 50 minutes. The reaction mixture was concentrated in vacuo and re-concentrated in toluene and hexane to give the title compound as a white solid.

h) 2-[(4-CBZ-aminoiminomethyl)benzoyl]amino]-6-(benzyloxycarbonylmethoxy)-1-tetralone To a mixture of 2-amino-6-(benzyloxycarbonylmethoxy)-1-tetralone hydrochloride (0.17 g, 0.47 mmol), 4-(CBZ-aminoiminomethyl)benzoic acid (0.14 g, 0.47 mmol), HOBT (0.082 g, 0.61 mmol) and EDC (0.11 g, 0.59 mmol) in dry DMF (9 mL), was added at 0° C. DIEA (0.087 g, 0.67 mmol) the reaction mixture was stirred at room temperature overnight under argon and then it was poured into a flask containing ice (20 g) and 5% sodium bicarbonate (1.8 mL). The white precipitate was filtered to give 0.22 g (79%) of a crude product. Silica gel chromatography (5% methanol/methylene chloride) gave the title compound (0.19 g, 68%) as a white solid.

i) 2-[(4-Aminoiminomethyl)benzoyl]amino]-6-(acetyloxy)-1-tetralone, trifluoroacetate salt A mixture of 2-[(4-CBZ-aminoiminomethyl)benzoyl]amino]-6-(benzyloxycarbonylmethoxy)-1-tetralone (0.18 g, 0.30 mmol) and 10% Pd/C (0.11 g) in glacial acetic acid (30 mL) was hydrogenated at 40 psi for 2.3 hours. The reaction mixture was filtered through Celite® to yield 50 mg of the crude product and the Celite® was again washed with a small amount of trifluoroacetic acid and acetic acid to afford 150 mg more of the desired product. The crude product was purified on reverse phase prep HPLC (C-18 column, acetonitrile/water (0.1% trifluoroacetic acid)) to give the title compound. MS (ES) m/e 382.0 (M+H)$^+$. Anal. Calcd. for $C_2H_{19}N_3O_5.C_2HF_3O_2.1/2H_2O$: C, 52.38; H, 4.20; N, 8.53. Found: C, 52.04; H, 4.45; N, 8.09.

EXAMPLE 3

2-[[(4-Aminoiminomethyl)benzoyl]amino)]-6-acetyloxy-1,2,3,4-tetrahydronaphthalene a) 6-Methoxy-1,2,3,4-tetrahydronaphthalene-2-oxime To the solution of hydroxylamine hydrochloride (2.9 g, 41.7 mmol) and sodium acetate (4.54 g, 55.4 mmol) in 18 mL of water was added a solution of 6-methoxy-3,4-dihydronaphthalene-2(1H)-one (6 g, 34 mmol) in 36 mL of ethanol. The mixture was stirred at room temperature for 30 minutes and then diluted with 100 mL of water and extracted with ether (3×100 mL). The ether extract was washed with water (50 mL), brine (50 mL), and dried over sodium sulfate. Filtration and removal of the solvent yielded 6.8 g of the crude product which was used without further purification.

b) 2-Amino-6-methoxy-1,2,3,4-tetrahydronaphthalene

The crude sample of 6-methoxy-1,2,3,4-tetrahydronaphthalene-2-oxime (6.8 g) was mixed with 5% Pd/C (1.25 g), methanol (120 mL), and concentrated hydrochloric acid (5 mL) and hydrogenated at an initial pressure of 50 psi for about 13 hours (added 0.66 g more of the catalyst after 11 hours). The mixture was filtered through Celite® and evaporated. The residue was dissolved in 0.5N hydrochloric acid (550 mL) and washed with ether (150 mL), basified with 10% sodium hydroxide to pH 8.5 and washed with methylene chloride (3×200 mL). The aqeous layer was again basified with 10% sodium hydroxide to pH 10.5 and extracted with methylene chloride (2×200 mL), dried over potassium carbonate, filtered and concentrated to give the title compound (2.28 g, 36%) as a brownish-green oil.

c) 2-Amino-6-hydroxy-1,2,3,4-tetrahydronaphthalene, hyhrobromide

A mixture of 2-amino-6-methoxy-1,2,3,4-tetrahydronaphthalene (2.17 g, 12.24 mmol) and 48% hydrobromic acid (50 mL) was heated at 120–130° C. for 2 hours. After removal of solvent, the solid residue was recrystallized in ethanol/ether to give the title compound (2.7 g, 90%), as a greyish-brown solid.

d) N-t-BOC-2-amino-6-hydroxy-1,2,3,4-tetrahydronaphthalene

A solution of di-tert-butyl dicarbonate (1.68 g, 7.7 mmol) in dioxane (12 mL) was added dropwise to a mixture containing 2-amino6hydroxy-1,2,3,4-tetrahydronaphthalene hyhrobromide (1.72 g, 7.0 mmol), 1N sodium hydroxide (18 mL) and dioxane (12 mL) at 0° C. The reaction mixture was stirred for 2 hours at 0° C. An additional 6 mL of 1N sodium hydroxide was added and the reaction was stirred for 1.25 hours at room temperature. The reaction mixture was concentrated to about 30 mL, diluted with 30 mL of water, and acidified with 1N sodium bisulfate to pH 8–9. The mixture was extrated with ethyl acetate (3×50 mL) and the organic layer was washed with water (2×20 mL), brine (10 mL) and dried over sodium sulfate. Silica gel chromatography (5% methanol/methylene chloride) gave the title compound (1.23 g, 66%).

e) N-t-BOC-2-amino-6-(benzyloxycarbonylmethoxy)-1,2,3,4-tetrahydronaphthalene

A mixture of N-t-BOC-2-amino-6-hydroxy-1,2,3,4-tetrahydronaphthalene (1.0 g, 3.8 mmol), potassium carbonate (0.52 g, 3.8 mmol) and acetone (30 mL) was refluxed under argon for 1 hour. The reaction mixture was cooled down to room temperature and a solution of benzyl 2-bromoacetate (1.04 g, 4.56 mmol) in acetone (10 mL) was added dropwise. The reaction mixture was stirred under reflux overnight, filtered and the filtrate was concentrated in vacuo. The residue was dissolved in methylene chloride (60 mL) and washed with water (10 mL), 5% sodium bicarbonate (15 mL), brine (10 mL) and dried over sodium sulfate. After filtration, the filtrate was concentrated in vacuo. After silica gel chromatography (1:4 ethyl actetate/hexane), the title compound (1.27 g, 81%) was isolated.

f) 2-Amino-6-(benzyloxycarbonylmethoxy)-1,2,3,4-tetrahydronaphthalene, hydrochloride To a solution of 4N hydrochloric acid/dioxane (30 mL) was added N-t-BOC-2-amino-6-(benzyloxy carbonyl methoxy)-1,2,3,4-tetrahydronaphthalene (1.26 g, 3.06 mmol). The reaction mixture was stirred at room temperature for 35 minutes and then it was concentrated to give the title compound (1.06 g, 100%) as a white solid.

g) [2-(4-CBZ-aminoiminomethyl)benzoylamino)]-6-(benzyloxycarbonylmethoxy)-1,2,3,4-tetrahydronaphthalene, hydrochloride To a mixture of 2-amino-6-(benzyloxycarbonylmethoxy)-1,2,3,4-tetrahydronaphthalene hydrochloride (0.70 g, 2.01 mmol), 4-(CBZ-aminoiminomethyl)benzoic acid (0.63 g, 2.11 mmol), HOBT (0.358 g, 2.65 mmol) in dry DMF (20 mL) was added at 0° C. DIEA (0.371 g, 2.88 mmol) and EDC (0.485 g, 2.55 mmol). The reaction mixture was stirred at room temperature overnight under argon and then it was poured into a flask containing ice (80 g) and 5% sodium bicarbonate (9 mL). The white precipitate was filtered to give 1.09 g (92%) of a crude product. Silica gel chromatography (3% methanol/methylene chloride) of the crude product (1.05 g) gave the title compound (0.94 g, 82%) as a white solid.

h) 2-[[(4-Aminoiminomethyl)benzoyl]amino)]-6-acetyloxy-1,2,3,4-tetrahydronaphthalene, bistrifluoroacetate A mixture of [2-(4-CBZ-aminoiminomethylbenzoylamino)]-6-(benzyloxycarbonylmethoxy)-1,2,3,4-tetrahydronaphthalene hydrochloride (0.62 g, 1.05 mmol) and 10% Pd/C (0.54 g) in acetic acid (20 mL), ethanol (20 mL), and ethyl acetate (25 mL) was hydrogenated starting at 46 psi for 4 hours. The reaction mixture was filtered through Celite® and concentrated in vacuo to give a crude product (0.37 g, 83%). Purification by reverse phase prep HPLC (C-18 column, acetonitrile/water (0.1% trifluoroacetic acid)) yieled analytically pure title compound. MS (ES) m/e 368 (M+H)$^+$, 366 (M−H)$^-$. Anal. Calcd. for $C_{20}H_{21}N_3O_4 \cdot 2C_2HF_3O_2$: C, 48.33; H, 4.06; N, 7.05. Found: C, 48.47; H, 4.24; N, 7.05.

EXAMPLE 4

N-4-[(Aminoiminomethyl)benzoyl]-6,7-diacetyloxy-1,2,3,4-tetrahydroisoquinoline a) N-4-cyanobenzoyl-6,7-dihydroxytetrahydroisoquinoline Commercially available 6,7-dimethoxytetrahydroisoquinoline was treated with 48% HBr according to a literature procedure [J. Med. Chem. (1976) 19, 127] to afford the bis-phenol. This material (8.71 g, 35.4 mmol) was treated with a THF solution of the NHS-ester of 4-cyanobenzoic acid (formed by reaction of 4-cyanobenzoic acid (5.01 g, 33.7 mmol) and N-hydroxysuccinimide (4.1 g, 34.6 mmol) over 90 minutes) and triethylamine (5.0 mL, 35.7 mmol) for 114 hours at room temperature. This reaction mixture was filtered with ethyl acetate rinses, washed with water, saturated sodium bicarbonate, brine and evaporated. The crude residue was dissolved in methanol (100 mL) and treated with concentrated ammonium hydroxide (20 mL) for 30 minutes. The solvents were stripped and a solid residue was rinsed with water and 3.13 g (32%) of product was collected by filtration.

b) N-4-caynobenzoyl-6,7-dicarbomethoxymethyloxy-1,2,3,4-tetrahydroisoquinoline

A mixture of N-4-cyanobenzoly-6,7-dihydroxytetrahydroisoquinoline (0.46 g, 1.57 mmol) and solid potassium carbonate (0.46 g, 3.33 mmol) in acetone/DMF 5:1 (12 mL) was heated to 60° C. for 1 hour; the mixture was cooled and methyl bromoacetate (0.44 mL, 4.55 mmol) was added dropwise. After 2.5 hours at room temperature, heating to 60° C. was resumed for 17 hours. The reaction mixture was cooled, evaporated, filtered through Celite® with ethylacetate rinses and re-evaporated to remove residual DMF. Flash chromatography (ethylacetate/hexanes) afforded the product (0.63 g, 91%).

c) N-4-[(aminoiminomethyl)benzoyl]6,7-dicarbomethoxymethyloxy-1,2,3,4-tetrahydroisoquinoline HCl gas was bubbled through a solution of N-4-cyanobenzoly-6,7-dicarbomethoxymethyloxy-1,2,3,4-tetrahydroisoquinoline (0.56 g, 1.28 mmol) in methanol (1 mL) and methylene chloride (4 mL) for 5 minutes. The flask was stoppered and cooled to 0° C. for 89 hours. The solvents were evaporated and the residue dissolved in methanol (5 mL) and treated with ammonium acetate (0.30 g, 3.85 mmol) and heated to reflux for 90 minutes. The solvents were evaporated and the residue triturated with ethylacetate to recover the product (0.49 g, 76%).

d) N-4-[(aminoiminomethyl)benzoyl]-6,7-diacetyloxy-1,2,3,4-tetrahydroisoquinoline hydrochloride The diester of N-4-[(aminoiminomethyl)benzoyl ]-6,7-dicarbomethoxymethyloxy-1,2,3,4-tetrahydroisoquinoline (0.39 g, 0.69 mmol) was dissolved in 10% aqueous acetic acid (15 mL) was heated to 105° C. for 42 hours. Removel of solvents afforded a solid release which was taken up in ethanol and treated with 10% HCl, filtered, then treated with 1N sodium hydroxide to pH to precipitate the desired product as a white solid. mp:>280° C. (dec). IR: 2960, 160, 1470 cm$^{-1}$. MS:MH$^+$428. $^1$HMR:9.36 (bs), 9.11 (bs), 7.86 (d), 7.66 (d), 6.7 (bs), 4.75–4.40 (m), 2.71 (m), 2.50 (m).

EXAMPLE 5

Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

EXAMPLE 6

Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

EXAMPLE 7

Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The foregoing is illustrative of the making and using of this invention. This invention, however, is not limited to the precise embodiments described herein, but encompasses all modifications within the scope of the claims which follow.

What is claimed is:
1. A compound of the formula:

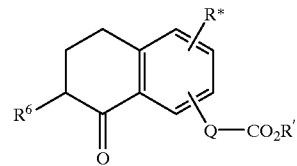

wherein:
Q is —O(CH$_2$)$_m$—, —NHC(O)CH$_2$—, or —C(O)NHCH$_2$—;
R* is H, Q—CO$_2$R', CO$_2$R', C$_{1-4}$alkyl, C$_{1-4}$alkoxy, C$_{1-4}$alkylthio, hydroxy, halo, NR'R', CN, CONR'R', CF$_3$ or ARC$_{0-4}$alkyl;
R$^6$ is W—(CR'$_2$)$_q$—Z—(CR'R$^7$)$_r$—U—(CR'$_2$)$_s$—V—;
Z is (CH$_2$)$_t$, Het, Ar or C$_{3-7}$cycloalkyl;
W is R'$_2$N, H$_2$NC(=NH), H$_2$NC(=NH)NH or (N);
U and V are absent or CO, CR'$_2$, C(=CR'$_2$), S(O)$_n$, O, NR', CR'OR', CR'(OR'')CR'$_2$, CR'$_2$CR'(OR''), C(O)CR'$_2$, CR'$_2$C(O), CONR', NR'CO, OC(O), C(O)O, C(S)O, OC(S), C(S)NR', NR'C(S), S(O)$_n$NR', NR'S(O)$_n$, N=N, NR'NR', NR'CR'$_2$, NR'CR'$_2$, CR'$_2$, OCR'$_2$, or CR'=CR', provided that U and V are not simultaneously absent;
R$^7$ is H, C$_{1-4}$alkyl or —NR'R'';
R' is H, C$_{1-6}$alkyl, C$_{3-7}$cycloalkyl-C$_{0-4}$ alkyl or Ar—C$_{0-4}$alkyl;
R'' is R', —C(O)R' or —C(O)OR$^{10}$;
R$^{10}$ is H, C$_{1-6}$alkyl or Ar—C$_{0-4}$alkyl;
m is 1 or 2;
n is 0 to 3;
q is 0 to 3;
r is 0 to 2;
s is 0 to 2; and
t is 0 to 2;
or a pharmaceutically acceptable salt thereof.
2. A compound according to claim 1 which is:
2-[[4-(aminoiminomethyl)benzoyl]amino]-6-acetyloxy-1-tetralone; or
2-(4-aminomethylbenzyl)-7-amidomalonyl-1-tetralone;
or a pharmacetuically acceptable salt thereof.
3. A pharmaceutical composition comprising a compound according to claim 1 and a pharmaceutically acceptable carrier.
4. A method for effecting inhibition of platelet aggregation which comprises administering a compound according to claim 1.
5. A method for treating stroke or a transient ischemia attack or myocardial infarction which comprises administering a compound according to claim 1.
6. A method for promoting reperfusion of an artery or vein and inhibiting reocclusion which comprises administering a fibrinolytic agent and a compound according to claim 1.

* * * * *